United States Patent [19]

Bouillon et al.

[11] 4,331,656

[45] May 25, 1982

[54] COMPOSITION AND PROCESS FOR REDUCING THE OILY APPEARANCE OF THE HAIR AND SKIN

[75] Inventors: Claude Bouillon, Eaubonne; Jean Maignan, Tremblay les Gonesse, both of France

[73] Assignee: L'Oreal, Paris, France

[21] Appl. No.: 115,556

[22] Filed: Jan. 21, 1980

[30] Foreign Application Priority Data

Jan. 29, 1979 [FR] France ................ 79 02188

[51] Int. Cl.$^3$ .................. A61K 7/00; A61K 7/06
[52] U.S. Cl. ........................ 424/70; 424/47; 424/63; 424/71; 424/365; 424/DIG. 1; 424/DIG. 2; 524/167; 524/173; 524/381
[58] Field of Search ............ 424/70, 71, 47, DIG. 1, 424/DIG. 2; 260/33.4 R

[56] References Cited

U.S. PATENT DOCUMENTS

| | | | |
|---|---|---|---|
| 3,966,398 | 6/1976 | Vanlerberghe et al. | 8/11 |
| 3,998,948 | 12/1976 | Vanlerberghe et al. | 424/170 |
| 4,058,629 | 11/1977 | Vanlerberghe et al. | 424/365 |

FOREIGN PATENT DOCUMENTS

| | | | |
|---|---|---|---|
| 2133991 | 12/1972 | France | 424/70 |
| 2133992 | 12/1972 | France | 424/70 |
| 63924 | 3/1973 | Luxembourg | 424/70 |

*Primary Examiner*—Alan L. Rotman
*Attorney, Agent, or Firm*—Cushman, Darby & Cushman

[57] ABSTRACT

A composition for treating oily hair or skin to reduce the oily appearance thereof comprises in an appropriate vehicle an active compound having the formula, $$(CH_2)_n \begin{matrix} S-R_1 \\ (O)_p \\ \\ S-R_1 \\ (O)_p \end{matrix}$$

wherein n is a whole number from 1–10 inclusive, p is 0, 1 or 2, and $R_1$ is $$-\underset{\underset{CH_2CO_2H}{|}}{CH}-CO_2H; \quad \text{(i)}$$

(ii) [phenyl ring with $R_2$ substituent]

wherein $R_2$ is $$-N\begin{matrix} R_3 \\ R_4 \end{matrix}$$

or $-CO_2H$ wherein $R_3$ and $R_4$ represent hydrogen, 2-hydroxy ethyl, 2-hydroxy propyl or 2,3-dihydroxy propyl; (iii) $-(CH_2-CHR_5)$ OH wherein $R_5$ is hydrogen, methyl or hydroxy methyl;

$$-CH_2-CH_2-N\begin{matrix} R_3 \\ R_4 \end{matrix} \quad \text{(iv)}$$

wherein $R_3$ and $R_4$ have the meanings given above; or (v)

$$-(CH_2)_q-\underset{\underset{CO_2H}{|}}{CH}-NH-A$$

wherein q is 1 or 2 and A represents hydrogen, acyl, succinoyl, nictinoyl or thenoyl; with the proviso that p is other than 0 and n is other than 2–4 when $R_1$ is (iv) or (v).

9 Claims, No Drawings

COMPOSITION AND PROCESS FOR REDUCING THE OILY APPEARANCE OF THE HAIR AND SKIN

The present invention relates to cosmetic compositions for treatment of oily hair or skin to reduce the oily appearance thereof.

Numerous cosmetic compositions for combatting in an effective manner against the oily appearance of the hair or skin have already been proposed. These compositions contain, principally, aminated thioethers such as the S-substituted derivatives of cysteine or cysteamine.

It has now been noted, in a surprising manner, that another class of thioethers can also be effectively employed as the active component in compositions for reducing the oily appearance of the hair and skin. This other class of thioethers comprises alkylene dithioethers and oxidation derivatives thereof.

Tests carried out by the applicants have shown that the cosmetic compositions of this invention, prepared with these alkylene dithioethers or oxidation derivatives thereof possess properties superior to those compositions obtained with other types of sulfur compounds.

The present invention more specifically relates to, as a new industrial product, a cosmetic composition containing as the principal active component thereof to reduce the oily appearance of the hair or skin at least one compound of the formula

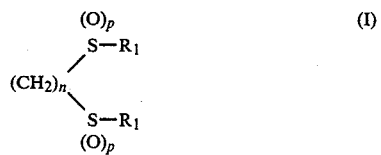 (I)

wherein
n is a whole number from 1 to 10 inclusive,
p is 0, 1 or 2, and
$R_1$ represents a member selected from the group consisting of

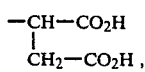 (i)

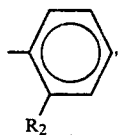 (ii)

wherein $R_2$ represents

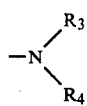

or —$CO_2H$ wherein $R_3$ and $R_4$ each independently represent hydrogen, 2-hydroxy ethyl, 2-hydroxy propyl or 2,3-dihydroxy propyl, (iii) —($CH_2$—$CHR_5$)OH, wherein $R_5$ represents hydrogen, methyl or hydroxy methyl,

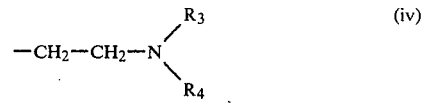 (iv)

wherein $R_3$ and $R_4$ have the meanings given above, and

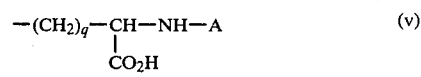 (v)

wherein q is 1 or 2 and A represents hydrogen, saturated or unsaturated acyl having 2–18 carbon atoms, succinoyl, nicotinoyl or thenoyl, with the proviso that p is other than 0 and n is other than 2–4 when $R_1$ represents either (iv) or (v), above.

When in formula (I) above, $R_1$ carries the amine function,

the active compounds can be provided in the form of salts obtained with an organic or mineral acid, for example, hydrochloric acid, malic acid, tartaric acid, camphosulfonic acid and the like.

Also when $R_1$ carries at least one free carboxylic acid function, the active compounds can be provided in the form of mono- or di-salts obtained with a mineral base such as, for example, alkali hydroxide or alkaline earth hydroxide, including NaOH and KOH and the like, or with an organic amine such as, for example, triethanolamine.

Representative active compounds useful in the compositions of the present invention for treating oily hair or skin to reduce the oily appearance thereof, include, in particular, the following compounds:

(1) 2,2'-methylenedithio diethylamine dihydrochloride,
(2) methylenedithio α,α'-disuccinic acid,
(3) 2,2'-ethylenedithio diethanol,
(4) 2,2'-ethylenedisulfinyl diethanol,
(5) 2,2'-ethylenedisulfonyl diethanol,
(6) 3,3'-ethylenedithio bis-(propanediol-1,2),
(7) 3,3'-ethylenedisulfinyl bis-(propanediol-1,2),
(8) 3,3'-ethylenedisulfonyl bis-(propendiol-1,2),
(9) 2,2'-methylenedithio dibenzoic acid,
(10) 2,2'-methylenedithio dianiline,
(11) 2,2'-ethylenedithio dianiline,
(12) 2,2'-ethylenedithio dibenzoic acid,
(13) 2,2'-ethylenedisulfinyl dibenzoic acid,
(14) 2,2'-ethylenedisulfinyl dianiline,
(15) 2,2'-(1,3-propanediyl dithio) diethanol,
(16) 2,2'-(1,3-propanediyl disulfinyl) diethanol,
(17) 2,2'-(1,3-propanediyl disulfonyl) diethanol,
(18) 3,3'-(1,3-propanediyl dithio) bis (propanediol-1,2),
(19) 3,3'-(1,3-propanediyl disulfinyl) bis (propanediol-1,2),
(20) 3,3'-(1,3-propanediyl disulfonyl) bis (propanediol-1,2),
(21) 2,2'-(1,3-propanediyl disulfinyl) diethylamine dihydrochloride,

(22) 2,2'-(1,3-propanediyl disulfonyl) diethylamine dihydrochloride,
(23) 2,2'-(1,3-propanediyl dithio) dianiline,
(24) 2,2'-(1,3-propanediyl dithio) dibenzoic acid,
(25) 2,2'-(1,4-butanediyl dithio) dibenzoic acid,
(26) 2,2'-(1,4-butanediyl dithio) diethanol,
(27) 3,3'-(1,4-butanediyl dithio) bis (propanediol-1,2),
(28) 2,2'-(1,4-butanediyl disulfinyl) diethanol,
(29) 2,2'-(1,4-butanediyl disulfonyl) diethanol,
(30) 3,3'-(1,4-butanediyl disulfinyl) bis (propanediol-1,2),
(31) 3,3'-(1,4-butanediyl disulfonyl) bis (propanediol-1,2),
(32) 3,3'-(1,5-pentanediyl dithio) bis (propanediol-1,2),
(33) 2,2'-(1,5-pentanediyl dithio) diethylamine dihydrochloride,
(34) 2,2'-(1,5-pentanediyl dithio) dianiline,
(35) 2,2'-(1,5-pentanediyl dithio) dibenzoic acid,
(36) 2,2'-(1,6-hexanediyl dithio) diethanol,
(37) 2,2'-(1,6-hexanediyl disulfinyl) diethanol,
(38) 3,3'-(1,6-hexenediyl disulfinyl) bis (propanediol-1,2),
(39) 3,3'-(1,6-hexanediyl disulfonyl) bis (propanediol-1,2),
(40) 3,3'-(1,6-hexanediyl dithio) bis (propanediol-1,2),
(41) 2,2'-(1,6-hexanediyl dithio) dianiline,
(42) 2,2'-(1,6-hexanediyl disulfinyl) dianiline,
(43) 2,2'-(1,6-hexanediyl dithio) dibenzoic acid,
(44) 2,2'-(1,6-hexanediyl disulfinyl) dibenzoic acid,
(45) 2,2'-(1,6-hexanediyl disulfonyl) diethanol,
(46) 2,2'-(1,6-hexanediyl dithio) diethylamine dihydrochloride,
(47) 3,3'-(1,6-hexanediyl dithio) dialanine
(48) 3,3'-(1,6-hexanediyl dithio) bis (2-acetamido propionic) acid,
(49) 1,6-hexanediyl dithio $\alpha,\alpha'$-disuccinic acid,
(50) 2,2'-(1,7-heptanediyl dithio) diethylamine dihydrochloride,
(51) 2,2'-(1,7-heptanediyl dithio) dianiline,
(52) 3,3'-(1,7-heptanediyl dithio) bis (2-acetamido propionic) acid,
(53) 3,3'-(1,7-heptanediyl dithio) bis (propanediol-1,2),
(54) 3,3'-(1,8-octanediyl disulfinyl) bis (propanediol-1,2),
(55) 2,2'-(1,8-octanediyl dithio) diethanol,
(56) 2,2'-(1,8-octanediyl dithio) diethylamine dihydrochloride,
(57) tetrakis N,N,N',N'-(2-hydroxy ethyl) 3,10-dithia dodecanediamine,
(58) bis-[N,N'-(2,3-dihydroxy propyl)] 3,10-dithia dodecanediamine,
(59) bis-[N,N'-(2,3-dihydroxy propyl)] 3,8-dithia decanediamine,
(60) bis-[N,N'-(2-hydroxy propyl)] 3,10-dithia dodecanediamine,
(61) 2,2'-(1,8-octanediyl dithio) dibenzoic acid,
(62) 2,2'-(1,8-octanediyl dithio) dianiline,
(63) 2,2'-(1,9-nonanediyl dithio) diethanol,
(64) 3,3'-(1,9-nonanediyl dithio) bis (propanediol-1,2),
(65) 2,2'-(1,9-nonanediyl dithio) diethylamine dihydrochloride,
(66) 2,2'-(1,10-decanediyl dithio) diethanol,
(67) 3,3'-(1,10-decanediyl dithio) bis (propanediol-1,2),
(68) 2,2'-(1,10-decanediyl disulfinyl) diethanol,
(69) 2,2'-(1,10-decanediyl disulfonyl) diethanol,
(70) 3,3'-(1,10-decanediyl disulfonyl) bis (propanediol-1,2),
(71) 3,3'-(1,10-decanediyl disulfinyl) bis (propanediol-1,2),
(72) 2,2'-(1,10-decanediyl dithio) diethylamine dihydrochloride,
(73) 2,2'-(1,10-decanediyl disulfinyl) diethylamine dihydrochloride,
(74) 2,2'-(1,10-decanediyl disulfonyl) diethylamine dihydrochloride,
(75) 2,2'-(1,10-decanediyl dithio) dianiline,
(76) bis [N,N'-(2,3-dihydroxy propyl)] 3,14-dithia hexadecanediamine.
(77) 2,2'-(1,10-decanediyl dithio) dibenzoic acid,
(78) 1,10-decanediyl dithio $\alpha,\alpha'$-disuccinic acid,
(79) 3,3'-(1,10-decanediyl dithio) bis (2-acetamido propionic) acid,
(80) 4,4'-(1,6-hexanediyl dithio) bis (2-acetamido butyric) acid,
(81) 4,4'-(1,10-decanediyl dithio) bis (2-acetamido butyric) acid,
(82) 4,4'-(1,6-hexanediyl dithio) bis (2-amino butyric) acid,
(83) 4,4'-(1,6-hexanediyl disulfinyl) bis (2-amino butyric) acid,
(84) 3,3'-(1,10-decanediyl dithio) dianiline,
(85) 4,4'-methylenedithio bis (2-amino butyric) acid,
(86) 3,3'-methylenedithio bis (2-hexadecamido propionic) acid,
(87) 4,4'-methylenedithio bis (2-acetamido butyric) acid,
(88) 2,2'-(1,10-decanediyl dithio) diethylammonium dimalate,
(89) 2,2'-(1,6-hexanediyl dithio) diethylammonium dimalate,
(90) 3,3'-methylenedithio bis (2-succinamido propionic) acid,
(91) 3,3'-methylenedithio bis (2-hexamido propionic) acid,
(92) 4,4'-methylenedithio bis (2-hexamido butyric) acid,
(93) 4,4'-methylenedithio bis (2-succinamido butyric) acid,
(94) 2,2'-(1,6-hexanediyl dithio) diethylammonium tartrate,
(95) 2,2'-(1,10-decanediyl dithio) diethylammonium tartrate,
(96) 3,3'-methylenedithio bis (2-propionamido propionic) acid,
(97) 3,3'-methylenedithio bis (2-tetradecanamido propionic) acid,
(98) 3,3'-methylenedithio bis (undecene(-10) 2-amido propionic) acid,
(99) 4,4'-methylenedithio bis (2-hexadecanamido butyric) acid,
(100) 4,4'-methylenedithio bis (2-propionamido butyric) acid, and
(101) 3,3'-methylenedithio bis (2-acetamido propionic) acid.

The cosmetic composition according to the present invention contains at least one active compound of formula I above, or one of its salts, in suspension or in solution, in water, in an alcohol (such as ethanol or isopropanol), in a hydroalcoholic solution, in an oil, in an emulsion or in a gel.

The concentration of the active compound, according to the invention, is generally between 0.1 and 20 weight percent, and preferably between 1 and 10 weight percent, based on the total weight of the composition.

A capillary composition, in accordance with the present invention, can contain the active compounds of formula I either singly, or in admixture, or even in a mixture with other compounds already known to combat against the oily and unaesthetic appearance of the hair.

The capillary composition, according to the present invention, can also contain components such as penetrating agents, perfumes or preservatives, which are generally employed in cosmetic compositions.

The cosmetic composition, according to the present invention, can also be provided as a dry shampoo, in the form of a powder or an aerosol, which shampoo composition does not contain a surfactant, and is used for application for dry hair.

This dry shampoo composition is permitted to remain in contact with the hair for a short period of time after application thereto. Subsequently, the hair is then brushed whereby the oily and unaesthetic appearance of the hair is eliminated or substantially reduced.

The cosmetic composition of this invention can also be provided in the form of a hair setting lacquer or lotion which contains at least one active compound, as defined above, in combination with, in an appropriate cosmetic vehicle, at least one conventional cosmetic resin.

Representative useful cosmetic resins include, in particular: polyvinylpyrrolidone, copolymers or vinylpyrrolidone and vinyl acetate, copolymers of vinyl acetate and an unsaturated carboxylic acid, such as crotonic acid, copolymers resulting from the polymerization of vinyl acetate, crotonic acid and an acrylic or methacrylic ester, copolymers resulting from the copolymerization of vinyl acetate and alkyl vinyl ether, and copolymers resulting from the copolymerization of vinyl acetate, crotonic acid and a vinyl ester of a long carbon chain acid or even of an allylic or methallylic ester of a long carbon chain acid, and the like.

The cosmetic resins contained in these hair setting lacquer or lotion compositions can also be colored polymers, that is, polymers containing in their macromolecular chain, some dye molecules which impart to the hair a color or a particular shade.

These hair setting lacquer or lotion compositions can also contain direct dyes for imparting a color or shade to the hair. They can also contain other components conventionally employed in cosmetic compositions used for fixing the hair in a particular state, such as penetrating agents, cationic compounds, preservatives, vitamins, proteins, more or less hydrolyzed peptides, starch or cellulose derivatives, surfactants, dyes, perfumes and the like.

The cosmetic vehicles useful for the production of these types of compositions, i.e. hair setting lacquers or lotions or even for hair styling compositions include those which are classically employed therein such as an alcohol or a hydroalcoholic solution.

An alcoholic or hydroalcoholic solution of the active compound and the cosmetic resin is often termed a hair setting lotion.

An alcoholic or hydroalcoholic solution of the resin and active compound, admixed with an appropriate amount of a liquified gaseous propellant and packaged under pressure in an aerosol container, is often termed a hair lacquer composition.

In these types of hair setting lotion or lacquer compositions, the amount of the active compound is generally between 0.1 and 10 weight percent, and preferably between 1 and 3 weight percent, while the amount of resin is between 0.1 and 10 weight percent, based on the total weight of the composition.

The cosmetic compositions according to the present invention can also be provided in the form of a treating shampoo having a liquid appearance, clear, opaque or pearly, or even the appearance of a cream or gel. This type of composition also effectively combats against the oily and unaesthetic appearance of the hair by eliminating or substantially reducing this oily appearance.

These shampoo compositions are essentially characterized by the fact that they contain at least one anionic, cationic, nonionic or amphoteric detergent in combination with at least one active compound of formula I.

Representative anionic detergents include, in particular, alkyl sulfates, alkyl ether sulfates, alkyl polyether sulfates, alkyl sulfonates (the alkyl groups having from 8–18 carbon atoms), sulfated monoglycerides, sulfoned monoglycerides, sulfated alkanolamides, sulfoned alkanolamides, fatty acid soaps, monosulfosuccinates of fatty alcohols, condensation products of fatty acids with isethionic acid, condensation products of fatty acids with methyl taurine, condensation products of fatty acids with sarcosine and condensation products of fatty acids with a protein hydrolyzate.

Representative cationic detergents include, in particular, long chain quaternary ammoniums, esters of fatty acids and amino alcohols, polyether amines and amine oxides.

Representative nonionic detergents include, in particular, esters of polyols and sugars, condensation products of ethylene oxide on fatty acids, on fatty alcohols, on long chain alkylphenols, on long chain mercaptans, on long chain amides, and polyethers of polyhydroxylated fatty alcohols.

Representative amphoteric detergents, include, for instance, asparagine derivatives, condensation products of monochloroacetic acid on imidazolines, alkylaminopropionates or betain derivatives.

These shampoo compositions contain, generally, from 0.1 to 15 weight percent, and preferably from 1 to 10 weight percent of the active compound. They also contain, for example, from 4 to 20 weight percent, and preferably from 5 to 10 weight percent, of a detergent in solution in an aqueous medium.

The shampoos, such as defined above, can also contain conventional cosmetic components such as perfumes and dyes. They can also contain thickening agents such as fatty acid alkanolamides, cationic polymers, such as copolymers of quaternized vinylpyrrolidone, cationic cellulosic polymers, cellulose derivatives such as carboxymethyl cellulose or hydroxy methyl cellulose, esters of long chain polyols and natural gums, so as to provide the ultimate composition in the form of a cream or gel.

These shampoo compositions can, finally, be provided in the form of a powder destined, either to be applied to wet hair, or to be solubilized in a given volume of water before washing the hair.

The shampoo compositions can also include dyes for coloring the hair.

In a general fashion, a satisfactory result is obtained by shampooing the hair weekly with a shampoo composition of this invention. This treatment diminishes and, in certain cases, suppresses the oily appearance of the hair, while at the same time assuring the normal care of the hair.

It has also been observed by the applicants that the active compounds as defined above can, in combination with an appropriate cosmetic vehicle, be topically applied to oily skin to reduce the oily appearance thereof.

Such compositions for application to the skin are provided in the form of creams, milks, gels, dermatological cakes or aerosol foams. These compositions can also be provided in the form of aqueous or hydroalcoholic lotions. They contain generally from 0.1 to 15 weight percent of at least one compound of formula I, and preferably from 1 to 5 weight percent.

Certain ones of the active compounds used in the compositions of the present invention are known; others can be very easily prepared using any one of methods A, B and C represented below:

Method A

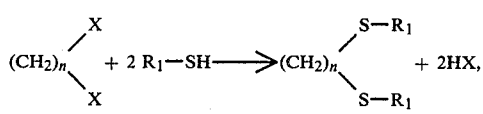

wherein X is halogen or sulfonate.

Method B

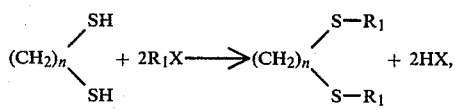

wherein X is halogen or sulfonate.

Method C

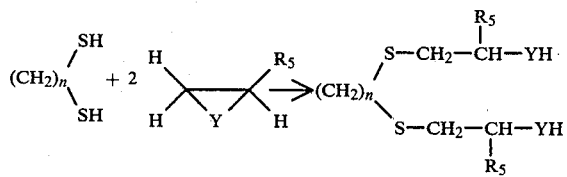

wherein Y is O or $NR_3$.

The reaction according to methods A and B is carried out in the presence of a base such as, for example, an alkali or alkaline earth hydroxide or carbonate, an alkali alcoholate or a tertiary amine such as triethylamine or triethanolamine.

The reaction is preferably carried out in a solvent medium, the latter being able to be water, an organic solvent (alcohol, dimethylformamide, chlorinated or aromatic hydrocarbons), or a mixture of such solvents.

When the process is carried out in accordance with Method C, the reaction can be effected in the absence of a base, and even, optionally, in the presence of an acid catalyst, especially in the case of non-substituted aziridine ($Y=NH$ and $R_5=H$).

The oxirane is selected from ethylene oxide, propylene oxide or even glycidol.

The aziridine can be either ethyleneimine or N-(2-hydroxy ethyl) aziridine.

The following non-limiting examples of cosmetic compositions, as well as examples of preparing the active compounds employed therein, are given to illustrate the invention. Unless otherwise specified, all parts and percentages are by weight.

EXAMPLES OF PREPARATION

Example 1

Preparation of 3,3'-ethylenedithio bis (propanediol-1,2)—Compound No. 6

Under a nitrogen atmosphere a solution in ethanol (200 ml) of 54.5 g (0.5 mole) of thioglycerol and 28 g (0.5 mole) of potash is agitated. There are then slowly added 47 g (0.25 mole) of 1,2-dibromo ethane. The reaction mixture is then heated to 50° C., with agitation, until the disappearance of the thiol (nitrocyanide test). After cooling, the mineral salts are filtered and the filtrate is concentrated to dryness under reduced pressure. The residue is then extracted with chloroform and the solution obtained is filtered and then concentrated again. The resulting residue is crystallized in acetonitrile, yielding 42 g of a white product melting at 67° C.

Analysis: $C_8H_{18}O_4S_2$: Calculated, %: C, 39.64; H, 7.48; S, 26.46; O, 26.41. Found, %: C, ;b 39.40; H, 7.47; S, 26.24; O, 26.38.

Examples 2–25

Table I,, below, lists the characteristics of compounds prepared in accordance with the same procedure as in Example 1 starting with a thiol $R_1SH$ and an alkylene dihalide, $X(CH_2)_nX$.

The resulting compounds which are liquid have been purified either by distillation each time that that was possible, or by washing with a solvent. The resulting compounds which are solid have been purified either by crystallization in an appropriate solvent (toluene, chloroform or acetonitrile) or by washing.

Compounds prepared starting with β-aminoethane-thiol have been treated directly by one equivalent of hydrochloric acid and isolated in the form of the hydrochloride thereof.

TABLE I

| EX. | Compound No. | $R_1$ | n | Yield, % | Melting or Boiling Point, °C. | Elemental Analysis | | Calculated, % Found, % |
|---|---|---|---|---|---|---|---|---|
| 2 | 3 | —$CH_2$—$CH_2OH$ | 2 | 90 | 66° | C 39.53 | H 7.74 | S 35.18 |
|  |  |  |  |  |  | 39.75 | 7.78 | 35.21 |
| 3 | 15 | —$CH_2$—$CH_2OH$ | 3 | 70 | 187° under 15mn | C 42.82 | H 8.21 | S 32.66 |
|  |  |  |  |  |  | 42.73 | 8.31 | 32.46 |
| 4 | 26 | —$CH_2$—$CH_2OH$ | 4 | 85 | 27° | C 45.68 | H 8.62 | S 30.49 |
|  |  |  |  |  |  | 45.50 | 8.58 | 30.26 |
| 5 | 36 | —$CH_2$—$CH_2OH$ | 6 | 70 | 43° | C 50.38 | H 9.30 |  |
|  |  |  |  |  |  | 50.53 | 9.40 |  |
| 6 | 18 | —$CH_2$—$CHOH$—$CH_2$—OH | 3 | 90 | * | *C 40.73 | H 7.97 | O 27.12 |
|  |  |  |  |  |  | 41.07 | 7.80 | 27.12 |
| 7 | 32 | —$CH_2$—$CHOH$—$CH_2$—OH | 5 | 75 | 29° | C 41.75 | H 7.64 | S 20.26 |
|  |  |  |  |  |  | 41.74 | 7.39 | 20.46 |
| 8 | 33 | —$CH_2$—$CH_2NH_2$ . HCl | 5 | 75 | 230° | C 36.59 | H 8.19 | N 9.48 |

TABLE I-continued

| EX. | Compound No. | $R_1$ | n | Yield, % | Melting or Boiling Point, °C. | Elemental Analysis | | Calculated, % Found, % | |
|---|---|---|---|---|---|---|---|---|---|
|   |   |   |   |   |   | 36.71 | 8.00 | 9.73 |   |
| 9 | 46 | —CH$_2$—CH$_2$NH$_2$ . HCl | 6 | 60 | 210° | C 38.82 | H 8.47 | N 9.05 |   |
|   |   |   |   |   |   | 38.96 | 8.25 | 8.94 |   |
| 10 | 72 | —CH$_2$—CH$_2$NH$_2$ . HCl | 10 | 65 | 230° | C 46.00 | H 9.37 | N 7.66 | S 17.54 |
|   |   |   |   |   |   | 45.88 | 9.31 | 7.84 | 17.42 |
| 11 | 10 | o-aminophenyl | 1 | 70 | non-distillable liquid | C 59.51 | H 5.38 | N 10.68 | S 24.44 |
|   |   |   |   |   |   | 59.33 | 5.65 | 10.70 | 24.62 |
| 12 | 11 | " | 2 | 75 | 73° | C 60.83 | H 5.83 | N 10.13 | S 23.20 |
|   |   |   |   |   |   | 60.90 | 5.85 | 10.24 | 23.17 |
| 13 | 23 | " | 3 | 70 | non-distillable liquid | C 62.03 | H 6.25 | N 9.64 | S 22.08 |
|   |   |   |   |   |   | 61.76 | 6.35 | 9.57 | 22.10 |
| 14 | 34 | " | 5 | 75 | non-distillable liquid | C 64.11 | H 6.96 | N 8.79 | S 20.13 |
|   |   |   |   |   |   | 64.27 | 6.79 | 8.67 | 19.98 |
| 15 | 41 | " | 6 | 75 | non-distillable liquid | C 65.01 | H 7.27 | N 8.42 | S 19.29 |
|   |   |   |   |   |   | 64.94 | 7.08 | 8.40 | 19.39 |
| 16 | 51 | " | 7 | 65 | non-distillable liquid | C 65.85 | H 7.66 | N 8.08 | S 18.51 |
|   |   |   |   |   |   | 66.01 | 7.60 | 7.89 | 18.45 |
| 17 | 62 | " | 8 | 60 | non-distillable liquid | C 66.62 | H 7.83 | N 7.77 | S 17.79 |
|   |   |   |   |   |   | 66.68 | 7.72 | 7.66 | 17.75 |
| 18 | 75 | " | 10 | 70 | non-distillable liquid | C 67.99 | H 8.30 | N 7.21 | S 16.50 |
|   |   |   |   |   |   | 68.28 | 8.03 | 7.00 | 16.40 |
| 19 | 12 | o-carboxyphenyl | 2 | 99 | 285° | C 57.46 | H 4.21 | S 19.17 |   |
|   |   |   |   |   |   | 57.41 | 4.50 | 19.02 |   |
| 20 | 24 | " | 3 | 99 | 220° | C 58.98 | H 4.62 | S 18.40 |   |
|   |   |   |   |   |   | 58.54 | 4.64 | 18.59 |   |
| 21 | 25 | " | 4 | 60 | 252° | C 59.64 | H 5.00 | S 17.62 |   |
|   |   |   |   |   |   | 59.69 | H 5.11 | 17.59 |   |
| 22 | 35 | " | 5 | 80 | 186° | C 60.61 | H 5.35 | S 17.03 |   |
|   |   |   |   |   |   | 60.38 | 5.55 | 17.02 |   |
| 23 | 43 | " | 6 | 98 | 218° | C 61.51 | H 5.67 | S 16.42 |   |
|   |   |   |   |   |   | 61.52 | 5.74 | 16.35 |   |
| 24 | 61 | " | 8 | 98 | 197° | C 63.12 | H 6.26 | S 15.32 |   |
|   |   |   |   |   |   | 62.97 | 6.46 | 15.58 |   |
| 25 | 77 | " | 10 | 98 | 186° | C 64.54 | H 6.77 | S 14.35 |   |
|   |   |   |   |   |   | 64.34 | H 6.71 | 14.20 |   |

*Product very hygroscopic, hydrates rapidly on contact with the atmosphere. The analysis corresponds to the hemihydrate.

Example 26

3,3'(1,4-butanediyl dithio) bis (propanediol-1,2), Compound No. 27

At ambient temperature and under a nitrogen atmosphere there is agitated a solution of 21.6 g (0.2 mole) of thioglycerol and 11.2 g (0.2 mole) of potash in methanol. 24.6 g (0.1 mole) of 1,4-butanediyl dimethanesulfonate are then slowly added, and the reaction mixture is brought to the boiling point of the solvent. Heating under reflux is followed for about 5 hours. The reaction mixture is then cooled and the mineral salts are filtered off. The resulting filtrate is concentrated under a vacuum. The oily residue is taken up with the use of heat in acetonitrile. After cooling and filtering, 19 g of white crystals melting at 54° C. are recovered.

Analysis: C$_{10}$H$_{22}$O$_4$S$_2$: Calculated, %: C, 44.42; H, 8.20. Found, %: C, 44.13; H, 8.17.

Using the same conditions, the following compounds are prepared:

Example 27

Compound No. 40

Initial reactants: thioglycerol and 1,6-hexanediyl dimethanesulfonate; Yield: 50%; Product—White crystals melting at 63° C.

Analysis: C$_{12}$H$_{24}$O$_4$S$_2$: Calculated, %: C, 48.29; H, 8.78. Found, %: C, 48.23; H, 8.60.

Example 28

Compound No. 67

Initial reactants: thioglycerol and 1,10-decanediyl dimethanesulfonate; Yield: 84%; Product—Whitish crystals, taken up in chloroform, melting at 94° C.

Analysis: C$_{16}$H$_{34}$O$_4$S$_2$: Calculated, %: C, 54.20; H, 9.66. Found, %: C, 54.13; H, 9.42.

Example 29

Compound No. 66

Initial reactants: β-mercaptoethanol and 1,10-decanediyl dimethanesulfonate; Yield: 76%; Product—Whitish crystals, taken up in a methanol-chloroform mixture, melting at 70° C.

Analysis: C$_{14}$H$_{30}$O$_2$S$_2$: Calculated, %: C, 57.09; H, 10.26; S, 21.77. Found, %: C, 57.25; H, 10.14; S, 21.66.

Example 30

Preparation of 3,3'-(1,6-hexanediyl dithio) bis (2-acetamido propionic) acid—Compound No. 48

A mixture of 10.96 g of 1,6-hexanediyl dimethanesulfonate and 13.04 g of N-acetyl cysteine in 100 ml of water is agitated under a nitrogen atmosphere at 50° C. There is then progressively added a solution of 5 N NaOH so that the pH of the reaction medium is maintained between 8.5 and 9.5. At the end of the reaction, verified by the absence of thiol groups (sodium nitrocyanide test), the mixture obtained is acidified to pH 2.5 with HCl. The product which precipitates is filtered, washed with water, and then crystallized in water. There are thus recovered 8.3 g of a white solid melting at 107° C.

Analysis: $C_{16}H_{28}N_2O_6S_2$: Calculated, %: C, 47.04; H, 6.91; N, 6.86; S, 15.70. Found, %: 47.03; H, 6.81; N, 6.82; S, 15.54.

Example 31

Preparation of 3,3'-(1,10-decanediyl dithio) bis (2-acetamido propionic) acid—Compound No. 79

This compound is prepared following the same procedures as those described in Example 30, using as the initial reactants, 1,10-decanediyl dimethanesulfonate and N-acetyl cysteine. The water is replaced by ethanol (50°). A white solid, melting at 120° C., is obtained for a 55% yield.

Analysis: $C_{20}H_{36}N_2O_6S_2$: Calculated, %: C, 51.70; H, 7.81; N, 6.03; S, 13.80. Found, %: C, 51.82; H, 7.90; N, 5.98; S, 13.92.

Example 32

Preparation of 3,3'-(1,6-hexanediyl dithio) dialanine—Compound No. 47

At 70° C., under nitrogen, a mixture of 137 g of 1,6-hexanediyl dimethanesulfonate and 175.5 g of cysteine-hydrochloride monohydrated in 1.5 l of water containing a little ethanol is agitated. There is then slowly added a solution of 5 N NaOH so that the pH of the reaction mixture is maintained between 8.5 and 9.5. At the end of the reaction the mixture is acidified to pH 5.2 with a solution of HCl. The precipitate is filtered, washed thoroughly with water, then dried and analyzed.

151 g of white product, melting with decomposition at a temperature greater than 250° C., is obtained.

Analysis: $C_{12}H_{24}N_2O_4S_2$: Calculated, %: C, 44.42; H, 7.45; N, 8.63; S, 19.76. Found, %: C, 44.07; H, 7.52; N, 8.55; S, 19.28.

Example 33

Compound No. 84

Compound No. 84 is obtained under the same conditions as those described in Example 32, with a yield of 98%. The resulting product is in the form of a white solid melting with decomposition above 250° C.

Analysis: $C_{16}H_{32}N_2O_4S_2$: Calculated, %: C, 50.49; H, 8.47; N, 7.36; S, 16.85. Found, %: C, 50.18; H, 8.13; N, 7.16; S, 16.91.

Example 34

Preparation of 2,2'-(1,6-hexanediyl dithio) diethylammonium tartrate—Compound No. 94

A solution of 7.5 g of hexanedithiol and 4.3 g of ethyleneimine in 150 ml of methanol is left to stand for several days, under a nitrogen atmosphere, at a temperature of 50° C. After the end of the reaction, the reaction mixture is concentrated under reduced pressure and the resulting oily residue is taken up in 60 ml of methanol at 50° C. under nitrogen; there is slowly added a solution of 6 g of tartaric acid in 75 ml of methanol and the reaction mixture is left to return to ambient temperature, with agitation. The solid precipitate is filtered, washed with methanol and recrystallized in a mixture of methanol and water.

After drying 12.5 g of white crystals melting at 170° C. are recovered.

Analysis: $C_{14}H_{30}N_2O_6S_2$: Calculated, %: C, 43.50; H, 7.82; N, 7.42; S, 16.59. Found, %: C, 43.21; H, 7.78; N, 7.51; S, 16.50.

Example 35

Compound No. 95

Employing the same conditions 2,2'-(1,10-decanediyl dithio) diethylammonium tartrate, Compound No. 95 is prepared using 11.3 g of decanedithiol as an initial reactant. 14 g of white crystals melting at 160° C. are recovered.

Analysis: $C_{18}H_{38}N_2O_6S_2$: Calculated, %: C, 48.84; H, 8.65; N, 6.33; S, 14.48. Found, %: C, 48.73; H, 8.55; N, 6.24; S, 14.44.

Example 36

Preparation of methylenedithio α,α'-disuccinic acid—Compound No. 2

A solution of 27 g (0.3 mole) of trioxymethylene and 90 g (0.6 mole) of α-mercaptosuccinic acid in 600 cm³ of formic acid is saturated with dry gaseous HCl at a temperature between 30°–40° C., under a nitrogen atmosphere.

After 12 hours of standing at ambient temperature, the reaction mixture is concentrated under reduced pressure and the residue is then recrystallized in acetonitrile. After filtering and drying, 38 g of whitish crystals melting at 125° C. are recovered.

Analysis: $C_9H_{12}O_8S_2$: Calculated, %: C, 34.61; H, 3.87. Found, %: C, 34.71; H, 4.23.

Examples 37–38

Compound Nos. 1 and 9 are prepared, in accordance with the same procedures as those described in Example 36, from, respectively, β-aminoethanethiol hydrochloride and thiosalicylicic acid, rather than the α-mercaptosuccinic acid of Example 36. The resulting products have the following characteristics:

Compound No. 1—white crystals melting at 191° C.

Analysis: $C_5H_{16}Cl_2N_2S_2$ Calculated, %: N, 11.71; S, 26.80. Found, %: N, 11.76; S, 27.01.

Compound No. 9—white solid melting at 265° C.

Analysis: $C_{15}H_{12}O_4S_2$: Calculated, %: C, 56.23; H, 3.77; S, 20.01. Found, %: C, 56.60; H, 3.94; S, 19.98.

Examples of Preparing Oxidation Derivatives of the Dithioethers of Formula I wherein:

(1) p=1—Examples 39–53 (see Table II, below).

There are slowly added, with agitation, 100 millimoles of $H_2O_2$ (110 volumes) to a solution of 50 millimoles of dithioether in 100 ml of acetic acid. The temperature of the reaction mixture is maintained lower than 30° C. At the end of the reaction (potassium iodide test), the reaction mixture is filtered if the oxidation derivative has crystallized in the medium, or concentrated to dryness.

The characteristics of the resulting products obtained are set forth in Table II;

(2) p=2—Examples 54–64 (see Table III, below).

There are slowly added, with good agitation, 200 millimoles of $H_2O_2$ (110 volumes) to a solution of 50 millimoles of dithioether in acetic acid. The temperature of the solution is maintained at about 50° C. When the reaction is finished, the oxidation derivative formed is precipitated with sulfuric ether or diisopropylic ether. The characteristics of the resulting products are set forth in Table III.

TABLE II

| Compound No. | $R_1$ | n | Oxidation Derivative of Compound No. | Yield % | Melting Point, °C. | Elemental Analysis | | Calculated, % Found, % |
|---|---|---|---|---|---|---|---|---|
| 4 | $HOCH_2-CH_2-$ | 2 | 3 | 80 | 102° | C 33.63 | H 6.58 | S 29.92 |
|   |   |   |   |   |   | 33.88 | 6.58 | 29.95 |
| 16 | " | 3 | 15 | 80 | 92° | C 36.82 | H 7.06 | S 28.09 |
|   |   |   |   |   |   | 36.60 | 7.05 | 28.21 |
| 19 | $HOCH_2-CHOH-CH_2-$ | 3 | 18 | 60 | Oil* | C 33.32 | H 7.46 | S 19.77 |
|   |   |   |   |   |   | 33.20 | 7.20 | 19.81 |
| 21 | $HCl \cdot H_2N-CH_2-CH_2-$ | 3 |   | 95 | 168° | C 28.09 | H 6.73 | N 9.36 |
|   |   |   |   |   |   | 28.03 | 6.74 | 9.37 |
| 28 | $HOCH_2-CH_2-$ | 4 | 26 | 80 | 152° | C 39.64 | H 7.49 | S 26.46 |
|   |   |   |   |   |   | 39.74 | 7.45 | 26.60 |
| 38 | $HOCH_2-CHOH-CH_2-$ | 6 | 40 | 60 | 135° | C 43.61 | H 7.93 | S 19.41 |
|   |   |   |   |   |   | C 43.66 | H 7.87 | S 19.28 |
| 71 | " | 10 | 67 | 75 | 105° | C 49.71 | H 8.86 |   |
|   |   |   |   |   |   | 49.84 | 9.02 |   |
| 7 | " | 2 | 6 | 50 | 163° | C 35.02 | H 6.61 | S 23.37 |
|   |   |   |   |   |   | 34.83 | 6.82 | 23.50 |
| 30 | " | 4 | 27 | 65 | Oil | C 39.71 | H 7.73 | S 21.20 |
|   |   |   |   |   |   | 39.61 | 7.35 | 21.08 |
| 37 | $HOCH_2-CH_2-$ | 6 | 36 | 70 | 117° | C 44.42 | H 8.20 | S 23.76 |
|   |   |   |   |   |   | 44.10 | 8.48 | 23.85 |
| 68 | " | 10 | 66 | 90 | 118° | C 51.49 | H 9.26 | S 19.64 |
|   |   |   |   |   |   | 51.75 | 9.20 | 19.83 |
| 13 | o-carboxyphenyl | 2 | 12 | 60 | 210° | C 52.44 | H 3.85 | S 17.50 |
|   |   |   |   |   |   | 52.43 | 3.68 | 17.30 |
| 44 | o-carboxyphenyl | 6 | 43 | 60 | 190° | C 54.52 | H 5.49 | S 14.55 |
|   |   |   |   |   |   | 54.94 | 5.27 | 14.66 |
| 14 | o-aminophenyl | 2 | 11 | 50 | 193° | C 54.52 | H 5.23 | S 20.79 |
|   |   |   |   |   |   | 54.35 | 5.29 | 20.90 |
| 42 | " | 6 | 41 | 60 |   | C 59.31 | H 6.64 | S 17.59 |
|   |   |   |   |   |   | 59.19 | 6.69 | 17.40 |

*This compound is a dihydrate.

TABLE III

| Compound No. | $R_1$ | n | Oxidation Derivative of Compound No. | Yield, % | Melting Point, °C. | Elemental Analysis | | Calculated, % Found, % |
|---|---|---|---|---|---|---|---|---|
| 5 | $HOCH_2-CH_2-$ | 2 | 3 | 60 | 86° | C 29.26 | H 5.73 | S 26.04 |
|   |   |   |   |   |   | 29.01 | 6.04 | 26.10 |
| 17 | " | 3 | 15 | 50 | 153° | C 32.29 | H 6.19 | S 24.63 |
|   |   |   |   |   |   | 32.28 | 6.13 | 24.82 |
| 20 | $HOCH_2-CHOH-CH_2-$ | 3 | 18 | 60 | 112° | C 33.74 | H 6.29 | S 20.02 |
|   |   |   |   |   |   | 33.50 | 6.13 | 19.59 |
| 22 | $HCl \cdot H_2N-CH_2-CH_2-$ | 3 |   | 60 | 250° | C 25.38 | H 6.08 | S 19.36 |
|   |   |   |   |   |   | 25.57 | 6.15 | 19.29 |
| 29 | $HOCH_2-CH_2-$ | 4 | 26 | 75 | 120° | C 35.02 | H 6.61 | S 23.37 |
|   |   |   |   |   |   | 35.51 | 6.62 | 23.23 |
| 31 | $HOCH_2-CHOH-CH_2-$ | 4 | 27 | 65 | 108° | C 35.92 | H 6.63 |   |
|   |   |   |   |   |   | 36.60 | 6.61 |   |
| 39 | " | 6 | 40 | 60 | 101° | C 39.76 | H 7.23 |   |
|   |   |   |   |   |   | 39.92 | 7.12 |   |
| 70 | " | 10 | 67 | 75 | 128° | C 45.91 | H 8.19 |   |
|   |   |   |   |   |   | 45.85 | 8.17 |   |
| 8 | " | 2 | 6 | 60 | 145° | C 31.36 | H 5.92 | S 20.93 |
|   |   |   |   |   |   | 31.40 | 5.93 | 20.93 |
| 45 | $HOCH_2-CH_2-$ | 6 | 36 | 65 | 94° | C 39.72 | H 7.33 | S 21.21 |
|   |   |   |   |   |   | 39.87 | 7.32 | 21.14 |
| 69 | " | 10 | 66 | 70 | 119° | C 46.90 | H 8.43 |   |
|   |   |   |   |   |   | 46.93 | 8.43 |   |

EXAMPLES OF COMPOSITIONS

Example 1

| Cream for oily skin | |
|---|---|
| 3,3'-(1,10-decanediyl disulfinyl) bis (propanediol-1,2) | 1.5g |
| Benzalkonium chloride | 0.3g |
| Glycol stearate | 1g |
| Cetyl alcohol | 4g |
| Stearate polyoxyethylenated with 20 moles of ethylene oxide | 6g |
| Isopropyl palmitate | 10g |
| Calophyllum oil | 1g |
| Preservative (parahydroxybenzoates) | 0.3g |
| Perfume, sufficient amount | |
| Sterile demineralized water, sufficient for | 100g |

With daily application of this cream, a marked improvement of the oily appearance of the skin is observed. The same results are achieved by replacing the above active compound with 3,3'-(1,6-hexanediyl dithio) bis (propanediol-1,2).

Example 2

Capillary lotion for Oily Hair

A capillary lotion, for use after shampooing, on wet hair and before setting the hair is prepared by admixing the following components:

| | |
|---|---|
| Copolymer of vinyl acetate/vinyl-pyrrolidone | 1.5g |
| 2,2'-methylenedithio diethylamine dihydrochloride | 1g |
| Perfume | 0.1g |
| Ethyl alcohol (25°), sufficient for | 100ml |

Example 3

| Milk for oily skin | |
|---|---|
| Methylenedithio α,α'-disuccinic acid | 2.8g |
| Crosslinked polyacrylic acid, sold under the trade name CARBOPOL 934 | 0.375g |
| Isopropyl ester of lanolin fatty acids | 1g |
| Oxyethylenated lanolin | 2.5g |
| Oxyethylenated cetylstearyl alcohol | 3g |
| Substituted alkylamide | 2g |
| Triethanolamine, sufficient for pH = 8 | |
| Methyl parahydroxy benzoate | 0.1g |
| Propyl parahydroxy benzoate | 0.1g |
| Water, sufficient for | 100ml |

Example 4

| Shampoo powder | |
|---|---|
| Sodium laurylsulfate | 40g |
| Condensation products of the fatty acids of copra with sodium isethionate, sold under the trade name "HOSTAPON K.A." | 39g |
| 1,10-decanediyl dithio ethanol | 10g |
| Perfume | 1g |

Example 5

| Styling gel, for daily use | |
|---|---|
| 3,3'-(1,4-buranediyl dithio) bis (propanediol-1,2) | 0.8g |
| Copolymer of vinylpyrrolidone/vinyl acetate | 2g |
| Oxyethylenated lanolin | 1g |
| Polyethylene glycol 300 | 5g |
| Methyl parahydroxy benzoate | 0.1g |
| Propyl parahydroxy benzoate | 0.1g |
| Perfume | 0.1g |
| Triethanolamine, sufficient for pH = 8 | |
| Water, sufficient for | 100ml |

Example 6

| Dermatological cake | |
|---|---|
| 3,3'-(1,10-decanediyl dithio) bis (propanediol-1,2) | 3g |
| Igepon A: sodium alkane sulfonate | 80g |
| Liquid cut of lanolin sold under the trade name "LANTROL" | 12g |
| Purcellin oil: branched esters of fatty acids | 2g |
| Chlorine containing antiseptic | 0.5g |
| Titanium dioxide | 2g |
| Perfume | 2.5g |

In this Example, the 3 g of the active compound can advantageously be replaced by 2 g of 2,2'-(1,6-hexanediyl disulfinyl) dianiline.

Example 7

| Milk for oily skin | |
|---|---|
| 2,2'-ethylenedisulfinyl dibenzoic acid | 1.6g |
| Crosslinked polyacrylic acid, sold under the trade name "CARBOPOL 934" | 0.375g |
| Isopropyl ester of lanolin fatty acids | 1g |
| Oxyethylenated lanolin | 2.5g |
| Oxyethylenated cetylstearyl alcohol | 3g |
| Substituted alkylamide | 2g |
| Triethanolamine, sufficient for pH = 8 | |
| Methyl parahydroxy benzoate | 0.1g |
| Propyl parahydroxy benzoate | 0.1g |
| Water, sufficient for | 100g |

Example 8

| Capillary lotion for oily hair | |
|---|---|
| Calcium pantothenate | 0.5g |
| 3,3'-methylenedithio bis (2-acetamido) propionic) acid | 0.4g |
| Potash, sufficient for pH = 4.5 | |
| Perfume | 0.1g |
| Ethyl alcohol (40°) sufficient for | 100ml |

Example 9

| Lotion for daily usage for the care of oily hair | |
|---|---|
| 3,3'-(1,6-hexanediyl dithio) bis (propanediol-1,2) | 0.4g |
| Pyridoxine camphosulfonate | 0.3g |
| Perfume | 0.1g |
| Coloring agent | 0.1g |
| Ethyl alcohol (50°), sufficient for | 100ml |

Example 10

Lacquer for Oily Hair

In accordance with the present invention, this lacquer is prepared by admixing the following components:

| | |
|---|---|
| Poly-(vinyl pyrrolidone-vinyl acetate) resin, sold under the trade name "E 335" | 10g |
| 3,3'-(1,4-butanediyl dithio) bis (propanediol-1,2) | 1g |
| Methyl cellosolve | 2g |
| Absolute ethyl alcohol, sufficient for | 100g |

To prepare a lacquer for oily hair, 30 g of the above solution are packaged in an aerosol container together with 49 g of trichlorofluoromethane and 21 g of dichlorodifluoromethane.

Example 11

| Pearly liquid shampoo composition | |
|---|---|
| Sodium lauryl sulfate oxyethylenated with 2.2 moles of ethylene oxide | 9g |
| Sodium monolauryl sulfosuccinate | 1g |
| Polyethylene glycol distearate | 2g |
| Lauryl diethanolamide | 2g |
| Methylenedithio α,α'-disuccinic acid | 6g |
| Potash, sufficient for pH = 7.5 | |
| Perfume | 0.3g |
| Water, sufficient for | 100g |

In this Example, the 6 g of the active compound can advantageously be replaced by 3 g of 2,2'-(1,6-hexanediyl dithio) dibenzoic acid.

Example 12

| Cream shampoo | |
|---|---|
| Sodium lauryl sulfate | 12g |
| Condensation products of the fatty acids of copra with methyltaurine, a paste sold under the trade name "HOSTAPON C.T." | 40g |
| Lauryl monoethanolamide | 2g |
| Glycerol monostearate | 4g |
| 3,3'-(1,6-hexanediyl disulfonyl) bis (propanediol-1,2) | 3.5g |
| Perfume | 0.2g |
| Lactic acid, sufficient for pH = 6.5 | |
| Water, sufficient for | 100g |

Example 13

| Treating lotion for the skin | |
|---|---|
| 3,3'-(1,10-decanediyl disulfinyl) bis (propanediol-1,2) | 1.5g |
| Benzalkonium chloride | 0.2g |
| Ethyl alcohol | 13ml |
| Polyethylene glycol | 10g |
| Perfume, sufficient amount | |
| Soluble coloring agents, sufficient amount | |
| Sterile demineralized water, sufficient for | 100g |

Example 14

| Cream for oily hair | |
|---|---|
| Polyoxyethylenated stearate, sold under the trade name "MYRJ 49" | 3g |
| Glycerol monostearate | 4g |
| Cetyl alcohol | 7g |
| Petrolatum oil | 8g |
| Isopropyl myristate | 5g |
| 2,2'-(1,4-butanediyl dithio) diethanol | 12g |
| Methyl parahydroxy benzoate | 0.3g |
| 1% solution of crosslinked polyacrylic acid sold under the trade name "CARBOPOL 941" | 40g |
| Triethanolamine, sufficient for pH = 6.5 | |
| Water, sufficient for | 100g |

This cream is applied to the scalp after shampooing. The cream is lightly massaged into the hair and is permitted to remain in contact therewith for about 15 minutes. Thereafter, the hair is rinsed.

In this Example, the active compound can advantageously be replaced by the same amount of Compound No. 40.

Example 15

| Clear liquid shampoo | |
|---|---|
| Lauryl alcohol polyethoxylated with 12 moles of ethylene oxide | 13g |
| Copra diethanolamide | 4g |
| Copolymer of quaternized vinyl pyrrolidone, sold under the trade name "GAFQUAT 755" | 0.4g |
| 3,3'-(1,6-hexanediyl disulfonyl) bis (propanediol-1,2) | 2g |
| Perfume | 0.2g |
| Water, sufficient for | 100ml |

Example 16

Liquid shampoo

A liquid shampoo (to be left on the hair for 5 minutes before the final rinse) is prepared by admixing:

| | |
|---|---|
| Lauryl alcohol polyglycerolated with 4 moles of glycerol | 15g |
| Copolymer of quaternized vinyl pyrrolidone, sold under the trade name "GAFQUAT 755" | 0.4g |
| 3,3'-(1,6-hexanediyl dithio) bis (propanediol-1,2) | 5g |
| Polyethoxylated alkylamine, sold under the trade name "ETHOMEEN 18/15" | 0.8g |
| Lactic acid, sufficient for pH = 6 | |
| Perfume, sufficient amount | |
| Water, sufficient for | 100ml |

Example 17

| Lotion for oily skin | |
|---|---|
| 2,2'-methylenedithio diethylamine dihydrochloride | 1.4g |
| Di-isobutylcresoxyethoxyethyl dimethyl benzylammonium chloride | 0.3g |
| Salicylic acid | 0.2g |
| Polyethyleneglycol tert-dodecyl thioether | 0.1g |
| Miranol C2M (2-hydroxyethyl carboxy methyl alkyl imidazolinium) | 10g |

-continued

| Lotion for oily skin | |
|---|---|
| Perfume, sufficient amount | |
| Sterile demineralized water, sufficient for | 100g |

Example 18

| Mask for oily skin | |
|---|---|
| 2,2'-(1,10-decanediyl disulfinyl) diethanol | 4g |
| Gelatin | 1g |
| Gum tragacanth | 1g |
| Bentonite | 4g |
| Kaolin | 26g |
| Titaniun dioxide | 2g |
| Camphor | 0.04g |
| Coloring agent, sufficient amount | |
| Perfume, sufficient amount | |
| Sterile demineralized water, sufficient for | 100g |

Example 19

| Mask for treating oily skin | |
|---|---|
| 3,3'-(1,10-decanediyl dithio) bis (propanediol-1,2) | 2.5g |
| Oxyethylenated lanolin | 5g |
| Cetyl alcohol | 2g |
| Self-emulsifiable ethyleneglycol stearate | 7g |
| Petrolatum - Codex | 5g |
| Kaolin | 10g |
| Titanium oxide | 8g |
| Preservative | 0.3g |
| Water, sufficient for | 100g |

Example 20

Rinsing Lotion

A rinsing lotion for use in combatting against the oily appearance of the face is prepared by admixing the following components:

| | |
|---|---|
| 2,2'-(1,10-decanediyl dithio) diethanol | 1g |
| Propylene glycol | 2g |
| Sodium ethylenediamine tetraacetate | 0.1g |
| Ethyl alcohol | 16g |
| Methyl parahydroxy benzoate | 0.1g |
| Propyl parahydroxy benzoate | 0.1g |
| Perfume, sufficient amount | |
| Coloring agent, sufficient amount | |
| Water, sufficient for | 100g |

Example 21

| Cream for oily skin | |
|---|---|
| Ethyl alcohol | 5g |
| Isopropyl palmitate | 6g |
| Petrolatum oil | 6g |
| Polyoxyethylenated stearate | 4.5g |
| Glycerol monostearate | 2g |
| Preservative | 0.3g |
| 2,2'-(1,10-decanediyl dithio) diethylammonium dimalate | 1g |
| Sterile demineralized water, sufficient for | 100g |

The active compound of this Example can advantageously be replaced by the same amount of 2,2'-(1,6-hexanediyl dithio) diethylammonium dimalate.

Example 22

| Cream for oily skin | |
|---|---|
| Sorbitan monostearate polyoxyethylenated with 60 moles of ethylene oxide | 1g |
| Self-emulsifiable glyceryl monostearate | 6g |
| Stearyl alcohol | 1.5g |
| Stearic acid | 2g |
| Petrolatum oil | 15g |
| Sweet almond oil | 2g |
| Triethanolamine | 0.1g |
| 2,2'-(1,6-hexanediyl dithio) diethanol | 1g |
| Perfume | 0.4g |
| Water, sufficient for | 100g |

Example 23

| Lotion for oily skin | |
|---|---|
| 2,2'-ethylene disulfinyl dianiline | 0.5g |
| Pyrrolidone carboxylic acid (50%) | 3g |
| Water soluble neo purcellin: branched esters of fatty acids polyoxyethylenated with 4 moles of ethylene oxide | 0.5g |
| Perfume, sufficient amount | |
| Preservative | 0.2g |
| Water, sufficient for | 100g |

Example 24

| Lotion for oily skin | |
|---|---|
| Ethyldiethylene glycol | 10g |
| Ethanol | 9g |
| Trans-Sulfolanediol | 0.4g |
| 2,2'-(1,6-hexanediyl dithio) dibenzoic acid | 0.3g |
| Triethanolamine, sufficient for pH = 7.5 | |
| Water, sufficient for | 100g |

Example 25

| Cream for oily skin | |
|---|---|
| Sipol wax | 5g |
| Glycerol monostearate | 2g |
| Hydrogenated polyisobutylene | 3g |
| Petrolatum oil | 3g |
| Cetyl alcohol | 1g |
| Branched ester of fatty acids | 3.5g |
| Preservative | 0.3g |
| 3,3'-(1,6-hexanediyl disulfonyl) bis (propanediol-1,2) | 1.8g |
| Water, sufficient for | 100ml |

What is claimed is:

1. A cosmetic composition for treating oily hair or skin to reduce the oily appearance thereof comprising in an appropriate vehicle an effective amount of a compound having the formula

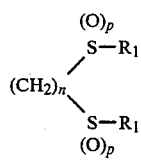

(I)

wherein
- n is a whole number from 1 to 10 inclusive;
- p is 0, 1 or 2; and
- $R_1$ represents —$(CH_2—CHR_5)$—OH wherein $R_5$ represents hydrogen, methyl or hydroxy methyl.

2. The cosmetic composition of claim 1 wherein said compound having formula (I) is selected from the group consisting of
(1) 2,2'-ethylenedithio diethanol,
(2) 2,2'-ethylenedisulfinyl diethanol,
(3) 2,2'-ethylenedisulfonyl diethanol,
(4) 3,3'-ethylenedithio bis-(propanediol-1,2),
(5) 3,3'-ethylenedisulfinyl bis-(propanediol-1,2),
(6) 3,3'-ethylenedisulfonyl bis-(propanediol-1,2),
(7) 2,2'-(1,3-propanediyl dithio) diethanol,
(8) 2,2'-(1,3-propanediyl disulfinyl) diethanol,
(9) 2,2'-(1,3-propanediyl disulfonyl) diethanol,
(10) 3,3'-(1,3-propanediyl dithio) bis(propanediol-1,2),
(11) 3,3'-(1,3-propanediyl disulfinyl) bis(propanediol-1,2),
(12) 3,3'-(1,3-propanediyl disulfonyl) bis(propanediol-1,2),
(13) 2,2'-(1,4-butanediyl dithio) diethanol,
(14) 3,3'-(1,4-butanediyl dithio) bis(propanediol-1,2),
(15) 2,2'-(1,4-butanediyl disulfinyl) diethanol,
(16) 2,2'-(1,4-butanediyl disulfonyl) diethanol,
(17) 3,3'-(1,4-butanediyl disulfinyl) bis(propanediol-1,2),
(18) 3,3'-(1,4-butanediyl disulfonyl) bis(propanediol-1,2),
(19) 3,3'-(1,5-pentanediyl dithio) bis(propanediol-1,2),
(20) 2,2'-(1,6-hexanediyl dithio) diethanol,
(21) 2,2'-(1,6-hexanediyl disulfinyl) diethanol,
(22) 3,3'-(1,6-hexanediyl disulfinyl) bis(propanediol-1,2)
(23) 3,3'-(1,6-hexanediyl disulfonyl) bis(propanediol-1,2),
(24) 3,3'-(1,6-hexanediyl dithio) bis(propanediol-1,2),
(25) 2,2'-(1,6-hexanediyl disulfonyl) diethanol,
(26) 3,3'-(1,7-hepthanediyl dithio) bis(propanediol-1,2),
(27) 3,3'-(1,8-octanediyl disulfinyl) bis(propanediol-1,2),
(28) 2,2'-(1,8-octanediyl dithio) diethanol,
(29) 2,2'-(1,9-nonanediyl dithio) diethanol,
(30) 3,3'-(1,9-nonanediyl dithio) bis(propanediol-1,2),
(31) 2,2'-(1,10-decanediyl dithio) diethanol,
(32) 3,3'-(1,10-decanediyl dithio) bis(propanediol-1,2),
(33) 2,2'-(1,10-decanediyl disulfinyl) diethanol,
(34) 2,2'-(1,10-decanediyl disulfonyl) diethanol,
(35) 3,3'-(1,10-decanediyl disulfonyl) bis(propanediol-1,2), and
(36) 3,3'-(1,10-decanediyl disulfinyl) bis(propanediol-1,2).

3. A cosmetic composition for treating oily hair or skin to reduce the oily appearance thereof comprising, in suspension or in solution, in water, in an alcohol or in a hydroalcoholic solution, an effective amount of a compound having the formula

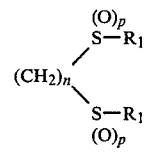

wherein
- n is a whole number from 1 to 10 inclusive;
- p is 0, 1 or 2; and
- $R_1$ represents —$(CH_2—CHR_5)$—OH wherein $R_5$ represents hydrogen, methyl or hydroxymethyl.

4. A cosmetic composition for treating oily hair or skin to reduce the oily appearance thereof comprising in an oil, suitable for application to the hair or skin, an effective amount of a compound having the formula

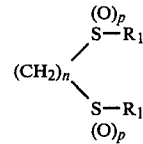

wherein
- n is a whole number from 1 to 10 inclusive;
- p is 0, 1 or 2; and
- $R_1$ represents —$(CH_2—CHR_5)$—OH wherein $R_5$ represents hydrogen, methyl or hydroxymethyl.

5. A cosmetic composition for treating oily hair or skin to reduce the oily appearance thereof comprising, in an emulsion or gel, an effective amount of a compound having the formula

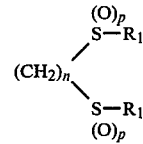

wherein
- n is a whole number from 1 to 10 inclusive;
- p is 0, 1 or 2; and
- $R_1$ represents —$(CH_2—CHR_5)$—OH wherein $R_5$ represents hydrogen, methyl or hydroxymethyl.

6. A cosmetic composition for treating oily hair or skin to reduce the oily appearance thereof comprising in an alcohol or hydroalcoholic solution, together with an effective amount of a cosmetic resin, an effective amount of a compound having the formula

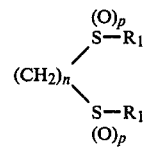

wherein
- n is a whole number from 1 to 10 inclusive;
- p is 0, 1 or 2; and
- $R_1$ represents —$(CH_2—CHR_5)$—OH wherein $R_5$ represents hydrogen, methyl or hydroxymethyl.

7. The cosmetic composition of claim 1 wherein said compound is present in an amount of 0.1 to 20 percent by weight based on the total weight of the composition.

8. The cosmetic composition of claim 1 wherein said compound is present in an amount of 1 to 10 percent by weight based on the total weight of the composition.

9. A process for treating oily hair or skin to reduce the oily appearance thereof comprising applying thereto an effective amount of the composition of claim 1.